US00PP25694P2

(12) United States Plant Patent
Scorza

(10) Patent No.: US PP25,694 P2
(45) Date of Patent: Jul. 14, 2015

(54) NECTARINE TREE NAMED 'NECTAFEST'

(50) Latin Name: ***Prunus persica* (L.) Batsch.**
Varietal Denomination: NECTAFEST

(71) Applicant: The United States of America, as represented by the Secretary of Agriculture, Washington, DC (US)

(72) Inventor: Ralph Scorza, Sheperdstown, WV (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 107 days.

(21) Appl. No.: 13/815,622

(22) Filed: Mar. 13, 2013

(51) Int. Cl.
*A01H 5/08* (2006.01)

(52) U.S. Cl.
USPC ..... Plt./192

(58) Field of Classification Search
CPC ..... A01H 5/0856; A01H 5/08
See application file for complete search history.

*Primary Examiner* — June Hwu
(74) *Attorney, Agent, or Firm* — Gail E. Poulos; John D. Fado; Lesley Shaw

(57) ABSTRACT

A new and distinct variety of yellow nectarine tree denominated 'NECTAFEST', having an upright growth form producing yellow, melting-flesh of excellent dessert-quality flavor, of large size for its ripening season, with approximately 80% red blush over a yellow ground color, ripening early in the growing season.

4 Drawing Sheets

Latin name of the genus and species of the plant claimed: 'NECTAFEST' is a nectarine tree that is *Prunus persica* (L.) Batsch.

Variety denomination: The new nectarine tree claimed is of the variety denominated 'NECTAFEST' *Prunus persica* (L.) Batsch.

BACKGROUND OF THE INVENTION

The present invention relates to a new and distinct variety of nectarine [*Prunus persica* (L.) Batsch] which is named 'NECTAFEST'. The new variety originated at the Appalachian Fruit Research Station, Agricultural Research Service, U.S. Department of Agriculture in Kearneysville, W. Va. and was identified as KV970512. It was selected in 2000 from a group of 19 seedlings that were produced from the open pollination of a seedling from the hand pollinated cross ('Flavortop' nectarine×'Italian Pillar') both non-patented. The new variety has been asexually reproduced at Adams County Nursery, Adams County Pa. by bud grafting on to 'Bailey' and 'Guardian' peach rootstocks. Testing for 7 years has shown that said variety maintains early ripening, high fruit quality, productivity, and maintains its upright tree form when bud-grafted onto these commonly used rootstocks. No aberrant types have appeared.

The growth habit of trees is upright. Fruit are melting flesh, dessert type. Flesh is yellow, flavorful and firm until full-ripe. Fruit have yellow ground color with red blush that covers approximately 80% of the fruit surface at maturity. Fruit size averages 64 mm in diameter with an average weight of 145 g. Fruit are sweet with a good balance of acidity. Brix of firm-ripe fruit averages 12 to 13° depending on date of harvest and environment. Fruit maintain firmness on the tree and in storage at levels comparable to commercial nectarine cultivars.

This new variety is distinct from it parents in its combination of upright growth habit, early season time of ripening, high fruit quality and large fruit size for its season of ripening.

SUMMARY OF THE INVENTION

A nectarine tree with upright growth habit and early fruiting producing high quality desert-type nectarines of large size for its early season of ripening.

BRIEF DESCRIPTION OF THE PHOTOGRAPHS

DETAILED BOTANICAL DESCRIPTION

Figure 1:
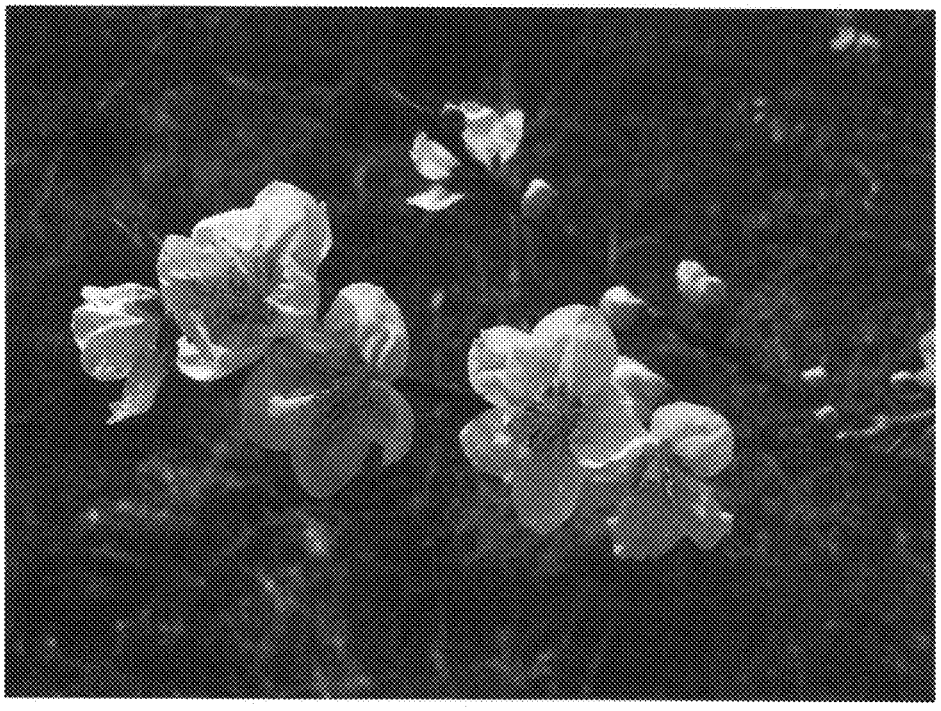
FIG. 1 is a full color photograph of 'NECTAFEST' flowers.
Figure 2:
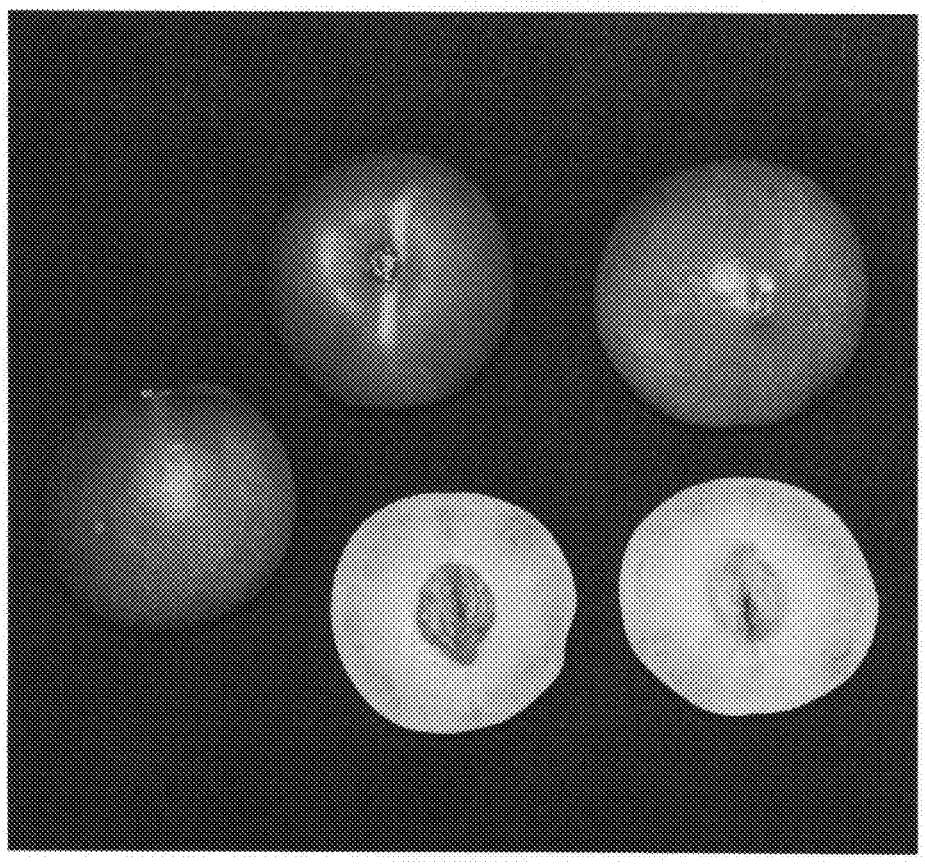
FIG. 2 is a full color photograph of 'NECTAFEST' fruit.
Figure 3:
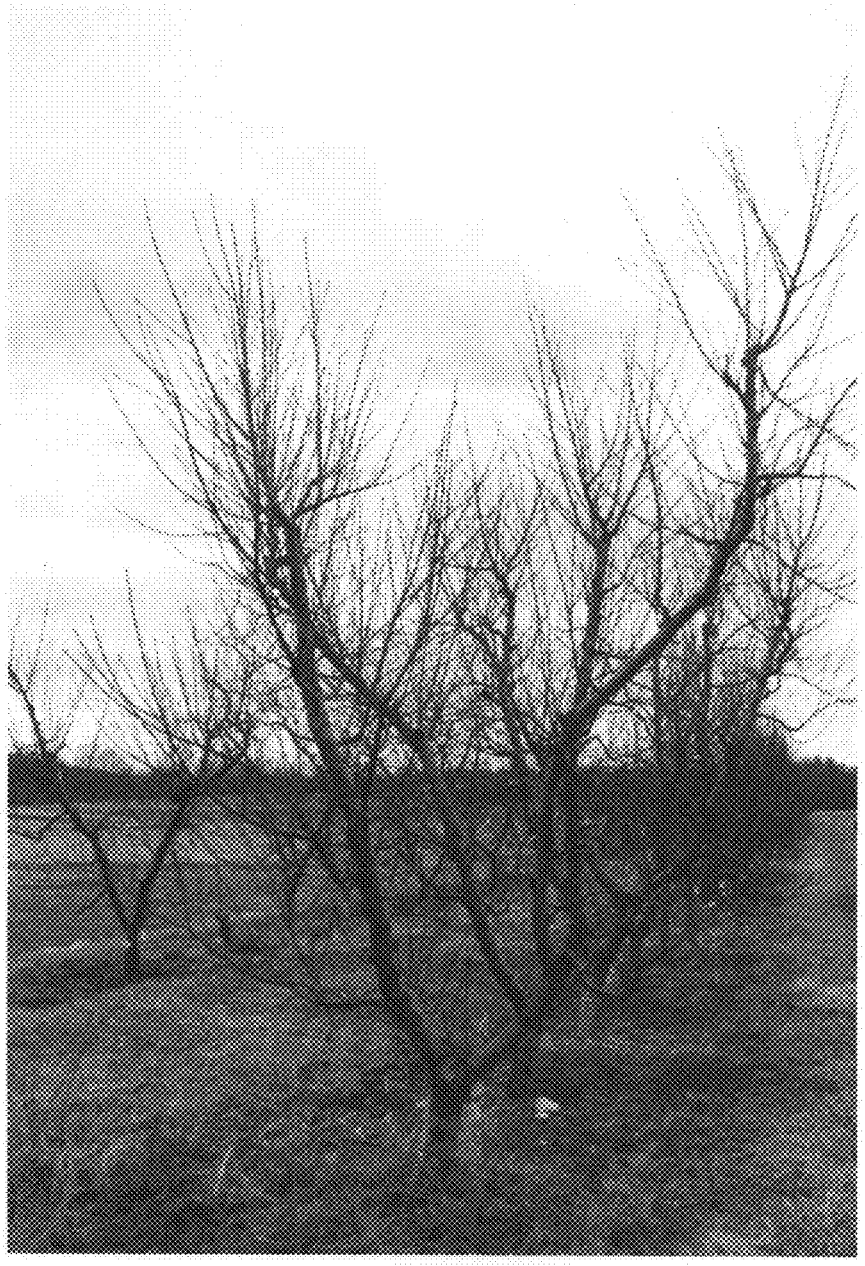
FIG. 3 is a full color photograph of 8 year old 'NECTAFEST' peach trees trained to the "Perpendicular V" system.
Figure 4:
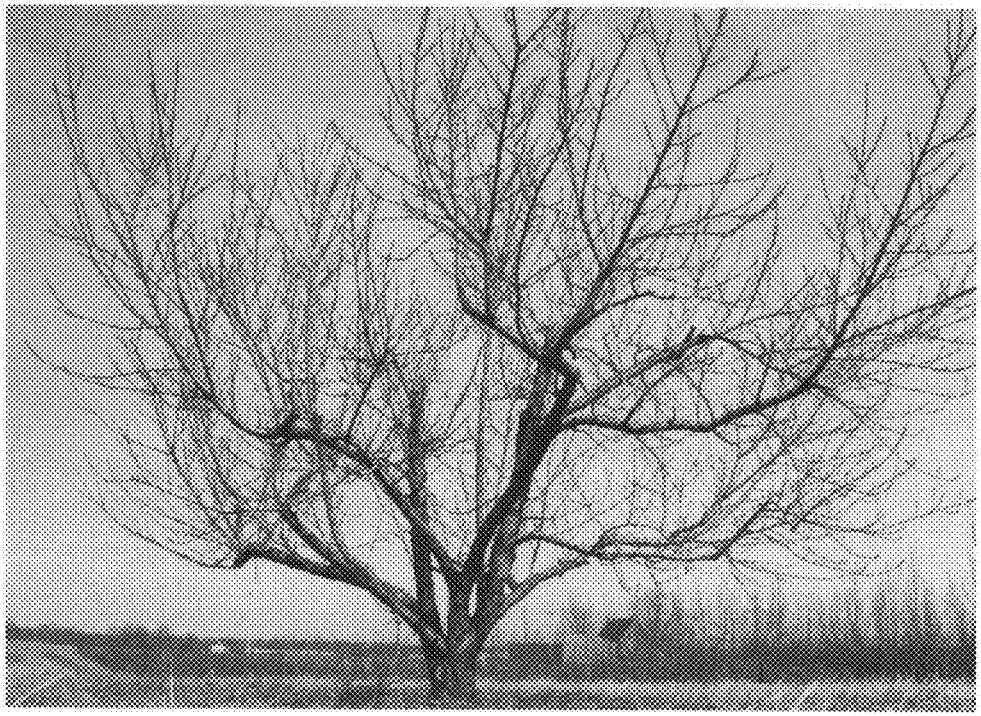
FIG. 4 is full color photograph of a 15 year old 'NECTAFEST' peach tree trained to standard open tree form.

The following is a detailed description of the botanical and pomological characteristics of the subject nectarine from specimens grown at Kearneysville, W. Va. Color data are presented in Royal Horticultural Society (R.H.S.) Colour Chart designations London (R.H.S.) ($4^{th}$ edition, 2001). Where dimensions, sizes, color, and other characteristics are given, it is to be understood that such characteristics are approximations of averages set forth as accurately as practicable.

Table 1 shows a comparison of yield of NECTAFEST with peach varieties 'Redhaven', 'John Boy', and 'White Lady' which ripen in the same early season.

TABLE 1

Yield comparison*

| Year | 'NECTAFEST' | 'Redhaven' | 'John Boy' | 'White Lady' |
|---|---|---|---|---|
| 2003 | 9 | 9 | 9 | 9 |
| 2004 | 4 | 8 | 7 | 6 |
| 2005 | 8 | 7 | 4 | 4 |
| 2011 | 8 | 8 | 9 | 7 |
| Average | 7.25 | 8 | 7.25 | 6.5 |

*Yield rating based on visual observation of generally 2-3 trees per cultivar. Rating scale 0 = no fruit; 7 = full commercial crop; 10 = fruit overload with some branches breaking.

Tree:

*Size.*—Canopy 3.125 meters high from the ground at 10 years of age. Canopy 5.4×4.7 m in width at 10 years of age.

*Vigor.*—Vigorous — average seasonal growth of shoots 37.4 cm with a diameter of 4.8 mm.

*Growth.*—Upright.

*Productivity.*—Good (see Table 1).

*Bearing.*—Self-fertile, regular bearing.

*Trunk.*—Size — diameter 21.4 cm (measured at 20 cm above ground level). Color — Brown N200D. Lenticels — color — Greyed Orange 167B. Lenticels length 6.1 mm. Lenticels width 2.3 mm. Lenticel density/cm$^2$ 1.5.

Branches:

*Lateral branches* (2-3 *years old*).—Size — Average diameter 12.0 mm. Angle from the supporting limb 54.3°. Bark color — Mostly Greyed-Orange 166C, some areas Brown Group N200C and N200D. Lenticels — color — greyed yellow 161B. Length 1.4 mm. Width 0.6 mm. Density 8.3/cm$^2$.

*Current season shoots.*—Length 37.4 cm. Diameter 4.8 mm. Color — shade side — Yellow Green N144D to 144D. Color — sun side — Greyed Purple 183A to 183B.

Leaves: Leaves are lanceolate, apex is acuminate, base is cuneate margin is crenate.

*Color.*—Adaxial — Green 137A to 137B. Abaxial — yellow green 147B.

*Petiole.*—Petiole is longitudinally grooved, color is yellow-green 144D tinged with greyed purple 184B. Average length 11.0 mm. Average width 1.8 mm. Average thickness 0.9 mm.

*Blade.*—Average length 15.2 cm. Average width 3.7 cm. Average thickness 0.2 mm.

*Leaf glands.*—Leaf glands are reniform, located on the petiole and/or base of the leaf blade. Color is N144, tinged with greyed purple 184B to 183A. Average number/leaf 3.9. Average length 1.7 mm. Average width 0.7 mm.

Flower buds:

*Flower bud density* (*buds/cm shoot*).—0.52.

*Color.*—Brown 200C to 200B with pubescence Grey 201D.

*Average length.*—5.37 mm.

*Average width.*—2.79 mm.

*Average # of buds per node.*—0.96.

*Average # of buds per cm.*—0.58.

*Average # bud scales.*—7.4.

*Average bud scale length* (*mm*).—4.4.

*Average bud scale width* (*mm*).—3.6.

*Bud scale color.*—Adaxial most scales greyed-orange 177A, some165A. Abaxial Greyed Purple 183C over Yellow Green 144B covered with pubescence White N155A.

Flowers:

*Petal.*—Broadly ovate. Margins are slightly wavy. Petals are slightly cupped longitudinally and transversally. Color adaxial — Red purple 62C. Color abaxial — Red Purple 73C becoming Red Purple 64 C at base of petal. As flower ages color becomes Red Purple 68C. Average petal length 20.9 mm. Average petal width 19.5 mm. Average flower diameter 36.45 mm.

*Stamen.*—Filament color N155D ageing to Red Purple 60B to C.

*Anther.*—Color Yellow Orange 14C. Average anther length 1.0 mm. Average anther width 0.70 mm. Average number/flower 45.8. Pollen color Yellow 13C.

*Filament.*—Average filament length 10.8 mm.

*Pistil.*—Overall average length of pistil 18.9 mm.

*Stigma.*—Color yellow-green 151A. Average diameter 1.2 mm.

*Style.*—Color Yellow Green 150B. Average diameter 0.50 mm.

*Ovary.*—Glabrous. Average height 1.8 mm. Average diameter 1.5 mm. Color yellow-green 151D.

*Hypanthium.*—Hypanthium diameter 6.9 mm. Hypanthium height 7.10 mm. Color Adaxial Orange group 28B. Abaxial yellow-Green 144D, veins 144A Greyed Purple 183C to 183A where exposed to sunlight.

*Caylx* (*sepals*).—Average number 5. Average sepal length 5.45 mm. Average sepal width 5.13 mm. Color Adaxial Yellow-Green 144B, streaked with Greyed Purple 183C. Abaxial Greyed-Purple 183C over Yellow-Green 14B. Sepals covered with fine hairs white N155A.

Fruit:

*Average weight.*—145.1g.

*Average length.*—61.6 mm.

*Average width.*—65.1 mm.

*Average thickness.*—61.9 mm.

*Average ° brix.*—13.5, medium sweetness with pleasing flavor.

*Flesh thickness.*—20.8 mm.

*Flesh color.*—Yellow-Orange 16B to 16C, some bleeding of pigment from skin into flesh tingeing flesh with red.

*Flesh fibers.*—Small, few, tender.

*Juiciness.*—Moderate.

*Epidermis ground color.*—Yellow 13C.

*Overcolor.*—Red 45A, some areas of Red 53A.

*Average pedicel length.*—7.8 mm.

*Average pedicel diameter.*—3.5 mm.

*Pedicel color.*—Yellow-Green N144D.

*Shape.*—Globose to slightly ovate, base-retuse, apex-rounded to slightly acute.

*Stalk cavity.*—Round with slight elongation in suture plane, moderate depth and diameter.

*Pit cavity.*—Slightly elongated in suture plane. Pit cavity color — Red Group 46A to 46B.

Stone: Freestone (stone readily separates from the surrounding flesh).

*Average stone* (*endocarp*) *weight.*—8 g.

*Average stone* (*endocarp*) *length.*—38.3 mm.

*Average stone* (*endocarp*) *width.*—20.8 mm.

*Average stone* (*endocarp*) *thickness.*—7.2 mm.

*Freestone.*—Ovoid shape, pointed, pits round to elongated.

*Stone color.*—Greyed-Orange group 165C to 165D tinged with Red Group 46A to 46B.

*Kernel cavity color* (*stone interior*).—Mostly Greyed-Orange 165B with some areas of 164B.

Kernel (seed): Broadly ovate.

*Average weight.*—0.44 g.

*Average length.*—17.1 mm.

*Average width.*—12.6 mm.

*Average thickness.*—4.3 mm.

*Average number kernels/stone.*—1.0.

*Kernel seed coat color.*—Greyed-Orange 167C with veins Greyed-Orange 164A.

Trees and fruit have not appeared to be more susceptible or less susceptible to insects or diseases than other nectarine cultivars grown in Kearneysville, W. Va.

Flower budbreak occurs in late March to mid-April in Kearneysville, W. Va. and lasts about 5 to 8 days. Both flowering time and duration depends upon weather conditions, with warmer temperatures advancing both. Vegetative budbreak starts about two to three days after flowering.

'NECTAFEST' is best adapted to USDA plant hardiness zone 6a (−10° F. to −5° F.) through 8a (10° F. to 15° F.). Depending upon specific favorable microclimates, this range may be extended in either direction.

I claim:

1. A new and distinct variety of yellow nectarine tree as illustrated and described, characterized by upright growth form, suitable for standard-density and high-density plantings; producing yellow, melting-flesh fruit of excellent dessert-quality flavor, a lively red skin color and ripening early in the growing season.

* * * * *